(12) United States Patent
O'Brien et al.

(10) Patent No.: US 6,555,535 B2
(45) Date of Patent: Apr. 29, 2003

(54) TRICYCLIC BIPHENYL SULFONAMIDE MATRIX METALLOPROTEINASE INHIBITORS

(75) Inventors: Patrick Michael O'Brien, Stockbridge, MI (US); Drago Robert Sliskovic, Saline, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/075,431

(22) Filed: Feb. 13, 2002

(65) Prior Publication Data
US 2002/0156071 A1 Oct. 24, 2002

Related U.S. Application Data
(60) Provisional application No. 60/268,754, filed on Feb. 14, 2001.

(51) Int. Cl.[7] ................. C07D 417/12; A61K 31/541
(52) U.S. Cl. .............. 514/228.2; 514/211.01; 514/365; 540/544; 544/60; 548/200; 548/201
(58) Field of Search ............. 544/60; 514/228.2, 514/211.01, 365; 540/544; 548/200, 201

(56) References Cited

U.S. PATENT DOCUMENTS

| 5,948,780 A | 9/1999 | Peterson, Jr. et al. ....... 514/255 |
| 6,008,243 A | 12/1999 | Bender et al. ............. 514/422 |

FOREIGN PATENT DOCUMENTS

| WO | WO 98/34918 | 8/1998 |
| WO | WO 00/06561 | 2/2000 |
| WO | WO 00/63165 | 10/2000 |
| WO | WO 01/63244 A1 | 8/2001 |

OTHER PUBLICATIONS

Creemers et al., PubMed Abstract (Circ. Res. 89(3):201–10), Aug. 2001.*

Morris et al., PubMed Abstract (Invasion Metastasis, 17(6):281–96), 1997.*

Rasmussen et al., Matrix Metalloproteinase Inhibition as a Novel Anticancer Strategy, Pharmacol. Ther., vol. 75, No. 1, pp. 69–75, 1997.*

Simone, Oncology: Introduction, Cecil Textbook of Medicine, 20th Edition, vol. 1, pp. 1004–10, 1996.*

Chambers et al., Changing Views of the Role of Matrix Metalloproteinases in Metastasis, Journal of the National Cancer Institute, vol. 89, No. 17, pp. 1260–1270, 1997.*

Montana, John, et al, "The design of selective non–substrate–based matrix metalloproteinase inhibitors", Current Opinion in Drug Discovery & Development, 2000; 3(4), pp 353–361.

Clark, Ian, et al, "Matrix metalloproteinase inhibitors in the treatment of arthritis", Current Opinions in Anti–inflammatory & Immunomodulatory Investigational Drugs, 2000; 2(1), pp 16–25.

Chen, James, et al, "Structure–Based Design of a Novel, Potent, and Selective Inhibitor for MMP–13 Utilizing NMR Spectroscopy and Computer–Aided Molecular Design", J. Am. Chem. Soc., 2000, 122; pp 9648–9654.

* cited by examiner

*Primary Examiner*—Deepak Rao
(74) *Attorney, Agent, or Firm*—Charles W. Ashbrook; Claude F. Purchase, Jr.

(57) ABSTRACT

Matrix metalloproteinase inhibitors are tricyclic sulfonamides of the Formula I

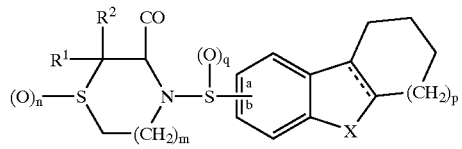

or a pharmaceutically acceptable salt thereof,
wherein $R^1$ and $R^2$ include hydrogen, alkyl, and substituted alkyl; $R^3$ is OH or NHOH; X is O or $S(O)_n$; n is 0, 1, or 2; p is 0, 1, 2, or 3; — is absent or a bond; and the sulfur atom bearing $(O)_q$ is bonded to the benzo ring at position a or position b.

13 Claims, No Drawings

TRICYCLIC BIPHENYL SULFONAMIDE MATRIX METALLOPROTEINASE INHIBITORS

CROSS-REFERENCE TO RELATED APPLICATIONS

This application claims benefit of priority from U.S. provisional application No. 60/268,754, filed Feb. 14, 2001.

FIELD OF THE INVENTION

This invention relates to a group of tricyclic sulfonamide compounds and derivatives which inhibit matrix metalloproteinase enzymes and thus are useful for treating diseases resulting from tissue breakdown, such as heart disease, multiple sclerosis, arthritis, atherosclerosis, and osteoporosis.

BACKGROUND OF THE INVENTION

Matrix metalloproteinases (sometimes referred to as MMPs) are naturally-occurring enzymes found in most mammals. Over-expression and activation of MMPs or an imbalance between MMPs and inhibitors of MMPs have been suggested as factors in the pathogenesis of diseases characterized by the breakdown of extracellular matrix or connective tissues.

Stromelysin-1 and gelatinase A are members of the matrix metalloproteinases (MMP) family. Other members include fibroblast collagenase (MMP-1), neutrophil collagenase (MMP-8), gelatinase B (92 kDa gelatinase) (MMP-9), stromelysin-2 (MMP-10), stromelysin-3 (MMP-11), matrilysin (MMP-7), collagenase 3 (MMP-13), TNF-alpha converting enzyme (TACE), and other newly discovered membrane-associated matrix metalloproteinases (Sato H., Takino T., Okada Y., Cao J., Shinagawa A., Yamamoto E., and Seiki M., *Nature*, 1994;370:61–65). These enzymes have been implicated with a number of diseases which result from breakdown of connective tissue, including such diseases as rheumatoid arthritis, osteoarthritis, osteoporosis, periodontitis, multiple sclerosis, gingivitis, corneal epidermal and gastric ulceration, atherosclerosis, neointimal proliferation which leads to restenosis and ischemic heart failure, and tumor metastasis. A method for preventing and treating these and other diseases is now recognized to be by inhibiting metalloproteinase enzymes, thereby curtailing and/or eliminating the breakdown of connective tissues that results in the disease states.

The catalytic zinc in matrix metalloproteinases is typically the focal point for inhibitor design. The modification of substrates by introducing zinc chelating groups has generated potent inhibitors such as peptide hydroxamates and thiol-containing peptides. Peptide hydroxamates and the natural endogenous inhibitors of MMPs (TIPs) have been used successfully to treat animal models of cancer and inflammation. MMP inhibitors have also been used to prevent and treat congestive heart failure and other cardiovascular diseases, U.S. Pat. No. 5,948,780.

There is a need to discover new low molecular weight compounds that are potent inhibitors of MMP enzymes without causing undesired side effects in animals. McClure recently described a series of arylsulfonyl hydroxamic acid derivatives that are said to be useful as broad spectrum MMP inhibitors (see WO 98/34918). We now have discovered a series of tricyclic sulfonamides that are especially potent MMP inhibitors with little or no toxic effects.

SUMMARY OF THE INVENTION

This invention provides a group of tricyclic sulfonamide compounds that are inhibitors of matrix metalloproteinase enzymes, and especially MMP-13. The invention is more particularly directed to compounds defined by Formula I

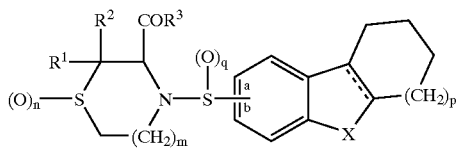

or a pharmaceutically acceptable salt thereof,
wherein:
the sulfur atom bearing $(O)_q$ is bonded to the benzo ring at position a or position b;
$R^1$ and $R^2$ independently are hydrogen, $C_1$–$C_6$ alkyl, $C_1$–$C_6$ alkoxy, $C_2$–$C_6$ alkenyl, $C_2$–$C_6$ alkynyl, or $(CH_2)_t$ aryl;
$R^3$ is NHOH or $OR^4$;
$R^4$ is H, $C_1$–$C_6$ alkyl, or $(CH_2)_t$ aryl;
X is O or $S(O)_n$;
each n and q independently are 0, 1, or 2;
m is 0, 1, or 2;
p is 0,1,2, or 3;
each t is an integer from 0 to 6; and
— is absent or is a bond.

Another invention embodiment is a compound of Formula II

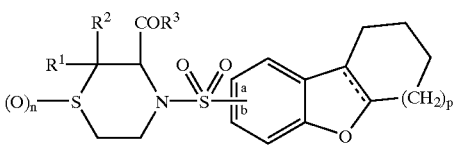

or a pharmaceutically acceptable salt thereof,
wherein $R^1$ and $R^2$ independently are H or $C_1$–$C_6$ alkyl;
$R^3$ is NHOH or OH;
the sulfonyl diradical is bonded to the benzo ring at position a or position b;
n is 0,1,or 2;
p is 1 or 2; and
— is absent or is a bond.

Another invention embodiment is a compound of Formula III

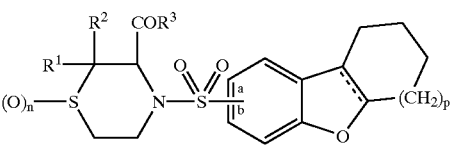

or a pharmaceutically acceptable salt thereof,
wherein $R^1$ and $R^2$ independently are H or $C_1$–$C_6$ alkyl;
$R^3$ is NHOH or OH;
the sulfonyl diradical is bonded to the benzo ring at position b;
n is 0, 1, or 2;
p is 1 or 2; and
— is absent or is a bond.

Another invention embodiment is a compound of Formulas II or III wherein $R^3$ is OH.

Another invention embodiment is a compound of Formulas II or III wherein $R^3$ is NHOH.

Another invention embodiment is a compound of Formula I, or a pharmaceutically acceptable salt thereof, selected from:

(S)-2,2-Dimethyl-4-(6,7,8,9-tetrahydro-dibenzofuran-3-sulfonyl)-thiomorpholine-3-carboxylic acid 1,1-dimethyl ester;

(S)-2,2-Dimethyl-4-(6,7,8,9-tetrahydro-dibenzofuran-3-sulfonyl)-thiomorpholine-3-carboxylic acid;

(S)-2,2-Dimethyl-4-(6,7,8,9-tetrahydro-dibenzofuran-3-sulfonyl)-thiomorpholine-3-carboxylic hydroxamide;

4-(2,3-Dihydro-1H-8-oxa-cyclopenta[a]indene-6-sulfonyl)-2,2-dimethyl-thiomorpholine-3-carboxylic acid hydroxyamide;

2,2-Dimethyl-4-(6,7,8,9-tetrahydro-5H-10-oxa-benzo[a]azulene-2-sulfonyl)thiomorpholine-3-carboxylic acid hydroxyamide;

4-(5,6,7,8,9,10-Hexahydro-11-oxa-cycloocta[a]indene-2-sulfonyl)-2,2-dimethyl-thiomorpholine-3-carboxylic acid hydroxyamide;

(S)-2,2-Dimethyl-1,1-dioxo-4-(6,7,8,9-tetrahydro-dibenzofuran-3-sulfonyl)-11$^6$-thiomorpholine-3-carboxylic acid hydroxyamide;

4-(2,3-Dihydro-1H-8-oxa-cyclopenta[a]indene-6-sulfonyl)-2,2-dimethyl-1,1-dioxo-11$^6$-thiomorpholine-3-carboxylic acid hydroxyamide;

2,2-Dimethyl-1,1-dioxo-4-(6,7,8,9-tetrahydro-5H-10-oxa-benzo[a]azulene-2-sulfonyl)-11$^6$-thiomorpholine-3-carboxylic acid hydroxyamide; and 4-(5,6,7,8,9,10-Hexahydro-11-oxa-cycloocta[a]indene-2-sulfonyl)-2,2-dimethyl-1,1-dioxo-11$^6$-thiomorpholine-3-carboxylic acid hydroxyamide.

A further embodiment of this invention is a pharmaceutical composition, comprising a compound of Formula I, or a pharmaceutically acceptable salt thereof, admixed with a pharmaceutically acceptable carrier, excipient, or diluent.

Another invention embodiment is a pharmaceutical composition, comprising a compound of Formula II, or a pharmaceutically acceptable salt thereof, admixed with a pharmaceutically acceptable carrier, excipient, or diluent.

Another invention embodiment is a pharmaceutical composition, comprising a compound of Formula III, or a pharmaceutically acceptable salt thereof, admixed with a pharmaceutically acceptable carrier, excipient, or diluent.

Another embodiment of this invention is a method for inhibiting an MMP enzyme in an animal, comprising administering to the animal an MMP enzyme inhibiting amount of a compound of Formula I, or a pharmaceutically acceptable salt thereof.

A further embodiment is a method for treating a disease mediated by an MMP enzyme, comprising administering to a patient suffering from such disease an effective amount of a compound of Formula I, or a pharmaceutically acceptable salt thereof.

Another invention embodiment is a method for treating a cancer, comprising administering to a patient suffering from such a disease an anticancer effective amount of a compound of Formula I, or a pharmaceutically acceptable salt thereof.

Another invention embodiment is a method for treating breast carcinoma, comprising administering to a patient suffering from such a disease an anticancer effective amount of a compound of Formula I, or a pharmaceutically acceptable salt thereof.

Another invention embodiment is a method for treating a rheumatoid arthritis, comprising administering to a patient suffering from such a disease an effective amount of a compound of Formula I, or a pharmaceutically acceptable salt thereof.

Another invention embodiment is a method for treating a osteoarthritis, comprising administering to a patient suffering from such a disease an effective amount of a compound of Formula I, or a pharmaceutically acceptable salt thereof.

Another invention embodiment is a method for treating a heart failure, comprising administering to a patient suffering from such a disease an effective amount of a compound of Formula I, or a pharmaceutically acceptable salt thereof.

Another invention embodiment is a method for treating a inflammation, comprising administering to a patient suffering from such a disease an effective amount of a compound of Formula I, or a pharmaceutically acceptable salt thereof.

Another embodiment of this invention is use of a compound of claim 1, or a pharmaceutically acceptable salt thereof, in the manufacture of a medicament for the treatment of a disease mediated by an MMP enzyme.

Another invention embodiment is use of a compound of claim 1, or a pharmaceutically acceptable salt thereof, in the manufacture of a medicament for the treatment of cancer.

Another invention embodiment is use of a compound of claim 1, or a pharmaceutically acceptable salt thereof, in the manufacture of a medicament for the treatment of arthritis.

Another invention embodiment is use of a compound of claim 1, or a pharmaceutically acceptable salt thereof, in the manufacture of a medicament for the treatment of rheumatoid arthritis.

Another invention embodiment is use of a compound of claim 1, or a pharmaceutically acceptable salt thereof, in the manufacture of a medicament for the treatment of osteoarthritis.

Another invention embodiment is use of a compound of claim 1, or a pharmaceutically acceptable salt thereof, in the manufacture of a medicament for the treatment of congestive heart failure.

DETAILED DESCRIPTION OF THE INVENTION

The compounds provided by this invention are those defined by Formula I. In Formula I, $R^1$–$R^4$ include "$C_1$–$C_6$ alkyl" groups. These are straight and branched carbon chains having from 1 to 6 carbon atoms. Examples of such alkyl groups include methyl, ethyl, isopropyl, tert-butyl, neopentyl, and n-hexyl. The alkyl groups can be substituted if desired, for instance with groups such as hydroxy, amino, alkyl, and dialkylamino, halo, trifluoromethyl, carboxy, nitro, and cyano.

"Alkenyl" means straight and branched hydrocarbon radicals having from 2 to 6 carbon atoms and one double bond and includes ethenyl, 3-buten-1-yl, 2-ethenylbutyl, 3-hexen-1-yl, and the like.

"Alkynyl" means straight and branched hydrocarbon radicals having from 2 to 6 carbon atoms and one triple bond and includes ethynyl, 3-butyn-1-yl, propynyl, 2-butyn-1-yl, 3-pentyn-1-yl, and the like.

"Cycloalkyl" means a monocyclic or polycyclic hydrocarbyl group such as cyclopropyl, cycloheptyl, cyclooctyl, cyclodecyl, cyclobutyl, adamantyl, norpinanyl, decalinyl, norbornyl, cyclohexyl, and cyclopentyl. Such groups can be substituted with groups such as hydroxy, keto, and the like. Also included are rings in which 1 to 3 heteroatoms replace carbons. Such groups are termed "heterocyclyl", which means a cycloalkyl group also bearing at least one heteroatom selected from O, S, or $NR_2$, examples being oxiranyl, pyrrolidinyl, piperidyl, tetrahydropyran, and morpholine.

"Alkoxy" refers to the alkyl groups mentioned above bound through oxygen, examples of which include methoxy, ethoxy, isopropoxy, tert-butoxy, and the like. In addition, alkoxy refers to polyethers such as —O—$(CH_2)_2$—O—$CH_3$, and the like.

"Alkanoyl" groups are alkyl linked through a carbonyl, ie, $C_1$–$C_5$—C(O)—. Such groups include formyl, acetyl, propionyl, butyryl, and isobutyryl.

"Acyl" means an R group that is an alkyl or aryl (Ar) group bonded through a carbonyl group, i.e., R—C(O)— where R is aryl, alkyl, heteroaryl, and the like. For example, acyl includes a $C_1$–$C_6$ alkanoyl, including substituted alkanoyl, wherein the alkyl portion can be substituted by $NR^4R^5$ or a carboxylic or heterocyclic group. Typical acyl groups include acetyl, benzoyl, and the like.

The alkyl, alkenyl, alkoxy, and alkynyl groups described above are optionally substituted, preferably by 1 to 3 groups selected from $NR^4R^5$, $CONR^4R^5$, $COC_1$–$C_6$ alkyl, phenyl, substituted phenyl, thio $C_1$–$C_6$ alkyl, $C_1$–$C_6$ alkoxy, hydroxy, carboxy, $C_1$–$C_6$ alkoxycarbonyl, halo, nitro, nitrile, cycloalkyl, and a 5- or 6-membered carbocyclic ring or heterocyclic ring having 1 or 2 heteroatoms selected from nitrogen, substituted nitrogen, oxygen, and sulfur. "Substituted nitrogen" means nitrogen bearing $C_1$–$C_6$ alkyl or $(CH_2)_n$Ph where n is 1, 2, or 3. Perhalo and polyhalo substitution is also embraced.

$R^4$ and $R^5$ independently include hydrogen, $C_1$–$C_6$ alkyl and $(CH_2)_t$ aryl, and $R^5$ can be $C_2$–$C_6$ alkenyl, $C_2$–$C_6$ alkynyl, aryl, $(CH_2)_t$ heteroaryl and $(CH_2)_t$ cycloalkyl, and $R^4$ and $R^5$ can be taken together with the nitrogen to which they are attached to complete a ring having 3 to 7 carbon atoms and 1, 2, or 3 heteroatoms selected from N, NR, O, and S.

Examples of $NR^4R^5$ groups include amino, methylamino, di-isopropylamino, acetyl amino, propionyl amino, 3-aminopropyl amino, 3-ethylaminobutyl amino, 3-di-n-propylamino-propyl amino, 4-diethylaminobutyl amino, and 3-carboxypropionyl amino. $R^4$ and $R^5$ can be taken together with the nitrogen to which they are attached to form a ring having 3 to 7 carbon atoms and 1, 2, or 3 heteroatoms selected from the group consisting of nitrogen, substituted nitrogen, oxygen, and sulfur. Examples of such cyclic $NR^4R^5$ groups include pyrrolidinyl, piperazinyl, 4-methylpiperazinyl, 4-benzylpiperazinyl, pyridinyl, piperidinyl, pyrazinyl, morpholinyl, and the like.

"Halo" includes fluoro, chloro, bromo, and iodo.

Examples of substituted alkyl groups include 2-aminoethyl, pentachloroethyl, trifluoromethyl, 2-diethylaminoethyl, 2-dimethylaminopropyl, ethoxycarbonylmethyl, 3-phenylbutyl, methanylsulfanylmethyl, methoxymethyl, 3-hydroxypentyl, 2-carboxybutyl, 4-chlorobutyl, 3-cyclopropylpropyl, pentafluoroethyl, 3-morpholinopropyl, piperazinylmethyl, and 2-(4-methylpiperazinyl)ethyl.

Examples of substituted alkynyl groups include 2-methoxyethynyl, 2-ethylsulfanyethynyl, 4-(1-piperazinyl)-3-(butynyl), 3-phenyl-5-hexynyl, 3-diethylamino-3-butynyl, 4-chloro-3-butynyl, 4-cyclobutyl-4-hexenyl, and the like.

Typical substituted alkoxy groups include aminomethoxy, trifluoromethoxy, 2-diethylaminoethoxy, 2-ethoxycarbonylethoxy, 3-hydroxypropoxy, 6-carboxyhexyloxy, and the like.

Further, examples of substituted alkyl, alkenyl, and alkynyl groups include dimethylaminomethyl, carboxymethyl, 4-dimethylamino-3-buten-1-yl, 5-ethylmethylamino-3-pentyn-1-yl, 4-morpholinobutyl, 4-tetrahydropyrinidylbutyl, 3-imidazolidin-1-ylpropyl, 4-tetrahydrothiazol-3-yl-butyl, phenylmethyl, 3-chlorophenylmethyl, and the like.

The terms "Ar" and "aryl" refer to unsubstituted and substituted aromatic groups. Heteroaryl groups have from 4 to 9 ring atoms, from 1 to 4 of which are independently selected from the group consisting of O, S, and N. Preferred heteroaryl groups have 1 or 2 heteroatoms in a 5- or 6-membered aromatic ring. Mono and bicyclic aromatic ring systems are included in the definition of aryl and heteroaryl. Typical aryl and heteroaryl groups include phenyl, 3-chlorophenyl, 2,6-dibromophenyl, pyridyl, 3-methylpyridyl, benzothienyl, 2,4,6-tribromophenyl, 4-ethylbenzothienyl, furanyl, 3,4-diethylfuranyl, naphthyl, 4,7-dichloronaphthyl, morpholinyl, indolyl, benzotriazolyl, indazolyl, pyrrole, pyrazole, imidazole, thiazole, and the like.

Preferred Ar groups are phenyl and phenyl substituted by 1, 2, or 3 groups independently selected from the group consisting of alkyl, alkoxy, thio, thioalkyl, halo, hydroxy, —$COOR^7$, trifluoromethyl, nitro, amino of the formula —$NR^4R^5$, and $T(CH_2)_mQR^4$ or $T(CH_2)_mCO_2R^4$ wherein m is 1 to 6, T is O, S, $NR^4$, $N(O)R^4$, $NR^4R^6Y$, or $CR^4R^5$, Q is O, S, $NR^5$, $N(O)R^5$, or $NR^5R^6Y$ wherein $R^4$ and $R^5$ are as described above, and $R^7$ is hydrogen, alkyl, or substituted alkyl, for example, methyl, trichloroethyl, diphenylmethyl, and the like. The alkyl and alkoxy groups can be substituted as defined above. For example, typical groups are carboxyalkyl, alkoxycarbonylalkyl, hydroxyalkyl, hydroxyalkoxy, and alkoxyalkyl.

The term "patient" means a mammal such as a human, a companion animal such as a dog or cat, and other animals such as horses, cattle, sheep, and the like.

The term "animal" means a mammal, including a human, dog, hamster, cat, horse, cow, pig, sheep, rat, mouse, rabbit, monkey, and guinea pig.

The term "cancer" as used herein includes all types of solid tumor diseases including colon cancer, breast cancer, lung cancer, prostate cancer, cancer of the oral cavity and pharynx, cancer of the stomach, small intestine, large intestine, rectum, liver, bone, connective tissue, skin, ovary, testis, bladder, kidney, brain, the central nervous system, and the like.

"Connective tissue disorders" means diseases resulting from degenerative cartilage loss following traumatic joint injury, osteoarthritis, osteoporosis, Paget's disease, periodontal disease, and gingivitis.

The phrases "therapeutically effective amount" and "effective amount" are synonymous unless otherwise indicated, and mean an amount of a compound of the present invention that is sufficient to improve the condition, disease, or disorder being treated. Determination of a therapeutically effective amount, as well as other factors related to effective administration of a compound of the present invention to a patient in need of treatment, including dosage forms, routes of administration, and frequency of dosing, may depend upon the particulars of the condition that is encountered, including the patient and condition being treated, the severity of the condition in a particular patient, the particular compound being employed, the particular route of administration being employed, the frequency of dosing, and the particular formulation being employed. Determination of a therapeutically effective treatment regimen for a patient is within the level of ordinary skill in the medical or veterinarian arts. In clinical use, an effective amount may be the amount that is recommended by the U.S. Food and Drug Administration, or an equivalent foreign agency.

The phrase "admixed" or "in admixture" means the ingredients so mixed comprise either a heterogeneous or homogeneous mixture. Preferred is a homogeneous mixture.

The phrases "pharmaceutical preparation" and "preparation" are synonymous unless otherwise indicated, and include the formulation of the active compound with encapsulating material as a carrier providing a capsule in which the active component, with or without other carriers, is surrounded by a carrier, which is thus in association with it. Similarly, cachets and lozenges are included. Pharmaceutical preparations are fully described below.

The phrase "anticancer effective amount" means an amount of invention compound, or a pharmaceutically acceptable salt thereof, sufficient to inhibit, halt, or cause regression of the cancer being treated in a particular patient or patient population. For example in humans or other mammals, an anticancer effective amount can be determined experimentally in a laboratory or clinical setting, or may be the amount required by the guidelines of the United States Food and Drug Administration, or equivalent foreign agency, for the particular cancer and patient being treated.

The phrase "antiarthritic effective amount" means an amount of invention compound, or a pharmaceutically acceptable salt thereof, sufficient to inhibit, halt, or cause regression of the arthritis being treated in a particular patient or patient population. For example in humans or other mammals, an antiarthritic effective amount can be determined experimentally in a laboratory or clinical setting, or may be the amount required by the guidelines of the United States Food and Drug Administration, or equivalent foreign agency, for the particular arthritis and patient being treated.

The phrase "MMP enzyme inhibiting amount" means an amount of invention compound, or a pharmaceutically acceptable salt thereof, sufficient to inhibit a matrix metalloproteinase enzyme, including a truncated form thereof, including a catalytic domain thereof, in a particular animal or animal population. For example in a human or other mammal, an MMP inhibiting amount can be determined experimentally in a laboratory or clinical setting, or may be the amount required by the guidelines of the United States Food and Drug Administration, or equivalent foreign agency, for the particular MMP enzyme and patient being treated.

It should be appreciated that the matrix metalloproteinases include the following enzymes:
MMP-1, also known as interstitial collagenase, collagenase-1, or fibroblast-type collagenase;
MMP-2, also known as gelatinase A or 72 kDa Type IV collagenase;
MMP-3, also known as stromelysin or stromelysin-1;
MMP-7, also known as matrilysin or PUMP-1;
MMP-8, also known as collagenase-2, neutrophil collagenase, or polymorphonuclear-type ("PMN-type") collagenase;
MMP-9, also known as gelatinase B or 92 kDa Type IV collagenase;
MMP-10, also known as stromelysin-2;
MMP-11, also known as stromelysin-3;
MMP-12, also known as metalloelastase;
MMP-13, also known as collagenase-3;
MMP-14, also known as membrane-type ("MT") 1-MMP or MT1-MMP;
MMP-15, also known as MT2-MMP;
MMP-16, also known as MT3-MMP;
MMP-17, also known as MT4-MMP;
MMP-18; and
MMP-19.
Other MMPs are known, including MMP-26, which is also known as matrilysin-2.

It should be appreciated that determination of proper dosage forms, dosage amounts, and routes of administration, is within the level of ordinary skill in the pharmaceutical and medical arts, and is described below.

The term "$IC_{50}$" means the concentration of test compound required to inhibit activity of a biological target, such as a receptor or enzyme, by 50%.

The phrase "catalytic domain" means the domain containing a catalytic zinc cation of the MMP enzyme, wherein the MMP enzyme contains two or more domains. A catalytic domain includes truncated forms thereof that retain at least some of the catalytic activity of the MMP or MMP-CD. For example, the collagenases, of which MMP-1, MMP-8, and MMP-13 are members, have been reported to contain a signal peptide domain, a propeptide domain, a catalytic domain, and a hemopexin-like domain (Ye Qi-Zhuang, Hupe D., Johnson L., *Current Medicinal Chemistry,* 1996;3:407418).

The phrase "a method for inhibiting an MMP enzyme" includes methods of inhibiting a full-length MMP, truncated forms thereof that retain catalytic activity, including forms that contain the catalytic domain of the MMP, as well as the catalytic domain of the MMP alone, and truncated forms of the catalytic domain of the MMP that retain at least some catalytic activity.

It should be appreciated that it has been shown previously (Ye Qi-Zhuang et al., supra., 1996) that inhibitor activity against a catalytic domain of an MMP is predictive of the inhibitor activity against the respective full-length enzyme.

The compounds to be used in the present invention can exist in unsolvated forms as well as solvated forms, including hydrated forms. In general, the solvated forms, including hydrated forms, are equivalent to unsolvated forms and are intended to be encompassed within the scope of the present invention. Some of the compounds may have chiral centers. The invention includes all racemates, pure enantiomers, and all geometric and positional isomers.

The compounds of Formula I, II and III are capable of further forming both pharmaceutically acceptable salts, including but not limited to acid addition and/or base salts, solvates and N-oxides. The compounds have one or more chiral centers, and thus exist as optical isomers, namely racemates, enantiomers, and the like. The compounds also exist as geometric and positional isomers, as well as polymorphs. All of these forms can be used in the method of the present invention and are provided as embodiments.

Pharmaceutically acceptable acid addition salts of the compounds of Formula II and III include salts derived form inorganic acids such as hydrochloric, nitric, phosphoric, sulfuric, hydrobromic, hydroiodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like, Also contemplated are the salts of amino acids such as arginate, gluconate, galacturonate, and the like; see, for example, Berge et al., "Pharmaceutical Salts," *J. of Pharmaceutical Science,* 1977;66:1–19.

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metal hydroxides, or of organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine; see, for example, Berge et al., supra., 1977.

The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

The compounds of the present invention can be formulated and administered in a wide variety of oral and parenteral dosage forms, including transdermal and rectal administration. All that is required is that an MMP inhibitor be administered to a mammal suffering from a disease in an effective amount, which is that amount required to cause an improvement in the disease and/or the symptoms associated with such disease. It will be recognized to those skilled in the art that the following dosage forms may comprise as the active component, either a compound of Formula II and/or III or a corresponding pharmaceutically acceptable salt or solvate of a compound of Formula II and/or III.

The invention compounds are prepared by methods well known to those skilled in the art of organic chemistry. The compounds of Formula I are prepared utilizing commercially available starting materials, or reactants that are readily prepared by standard organic synthetic techniques. A typical synthesis of the invention compounds of Formula I is shown in Scheme 1 below, which illustrates the coupling of a tricyclicsulfonyl halide to a suitably substituted thiomorpholine.

The first step in Scheme 1 comprises reacting a suitably substituted tricyclicsulfonyl chloride (compound 1) with a thiomorpholine carboxylic acid ester (compound 2). The compounds are combined in approximately equimolar quantities in a mutual solvent such as triethylamine and dichloromethane, and are stirred at a reduced temperature of about −5° C. to about 20° C. The reaction is generally substantially complete within about 2 to about 10 hours. The product, a tricyclicsulfonyl substituted thiomorpholine carboxylic acid ester (3), is isolated by diluting the reaction mixture with aqueous acid and extracting the product into an organic solvent such as ethyl acetate, chloroform, or dichloromethane. The product ester can be further purified, if desired, by standard methods such as chromatography, crystallization, distillation, and the like.

The tricyclicsulfonyl-thiomorpholine carboxylic acid esters are readily hydrolyzed to the carboxylic acids (4) of Formula I ($R^3$=OH) by standard methods, for example by reaction with an acid such as trifluoroacetic acid in a solvent such as anisole or dimethylsulfoxide.

Scheme 1 further illustrates the synthesis of hydroxamic acids (5) of Formula I ($R^3$=NHOH) by simply reacting the tricyclicsulfonyl-thiomorpholine carboxylic acid (4) with oxalyl chloride to give the corresponding acid chloride, and then reacting the acid chloride with hydroxylamine. The reaction generally is carried out in a mutual solvent such as tetrahydrofuran or dioxane, and is substantially complete within about 2 to 20 hours when carried out at a temperature of about 0° C. to about 25° C. The product hydroxamic acid (5) is readily isolated by extraction into an organic solvent such as diethyl ether or ethyl acetate, and concentration to dryness. The hydroxamic acids can be purified, if desired, by standard methods such as crystallization or chromatography over solid supports such as silica gel.

Scheme 1a illustrates the synthesis of sulfoxides and sulfones of Formula I (n=1 or 2, SO or $SO_2$). The tricyclicsulfonyl-thiomorpholine carboxylic acid esters (3) are reacted with an oxidizing agent such as peracetic acid or m-chloroperbenzoic acid. Reaction of the ester with one equivalent of oxidizing agent provides the invention sulfoxides (n=1, SO), and reaction with two equivalents or more effects complete oxidation to the corresponding sulfones (n=2, $SO_2$) (6).

As shown in Scheme 1a and discussed above, the carboxylic acid esters (of either a thiomorpholine sulfoxide or sulfone) (e.g., 6) is readily hydrolyzed to the carboxylic acids of Formula 1 (7), which are potent MMP inhibitors, and which can be readily converted to the invention hydroxamic acids (8). A synthetic path to compound 1, the substituted tricyclicsulfonyl chloride used in Scheme 1, is provided in Schemes 2 and 2a.

Scheme 2 provides a synthetic pathway to the substituted tricyclicsulfonyl chloride (compound 1) utilized in Scheme 1. As show in Scheme 2, a phenoxide is reacted with compound 9 to form an alcohol, compound 10, after appropriate workup. Preferably, the phenoxide is generated by reacting a solution of phenol in water and cesium carbonate. Alternatively, sodium phenoxide may be used in place of the phenol and cesium carbonate. Compound 10 is oxidized, preferably with a Jones Reagent to give compound 11. Compound 11 is then cyclized with an acid solution to give compound 12. Preferably, a mixture of phosphoric acid and sulfuric acid is utilized for the cyclization. Finally, compound 12 is sulfonated to form a sulfonic acid followed by replacement of the OH in the acid to form a sulfonyl chloride. Preferably, the sulfonation is accomplished by reaction of compound 12 with sulfur trioxide-DMF to form the sulfonic acid. The sulfonic acid is reacted with thionyl chloride to form compound 13.

A variation of scheme 2 is provided in scheme 2a. In Scheme 2a, compound 14 (cyclooctene oxide) is reacted with a phenoxide to from compound 15. Preferably, the phenoxide is sodium phenoxide in water. Alternatively, the phenoxide is generated by reacting a solution of phenol in water and cesium carbonate. Compound 15 is oxidized, preferably with a Jones Reagent to give compound 16. Compound 16 is hydrogenated to form compound 17. Preferably, hydrogenation is done under hydrogen gas with a palladium catalyst. Compound 17 is then cyclized with an acid solution to give compound 18. Preferably, a mixture of phosphoric acid and sulfuric acid is utilized for the cyclization. Finally, compound 18 is sulfonated to form a sulfonic acid followed by replacement of the OH in the acid to form a sulfonyl chloride. Preferably, the sulfonation is accomplished by reaction of compound 18 with chlorosulfonic acid to form the sulfonic acid. The sulfonic acid is reacted with thionyl chloride to form compound 19.

Any of the unsaturated compounds of Formula I (where — is a bond) can be readily hydrogenated to the corresponding saturated compound (where — is absent). Such hydrogenation reactions are typically carried out in the presence of hydrogen gas in a catalyst such as palladium or platinum, and generally in a solvent such as methanol or ethanol.

It should be appreciated that in the following schemes, groups $R_1$, $R_2$, and $R_3$ mean the groups of Formula I that are $R^1$, $R^2$, and $R^3$, respectively.

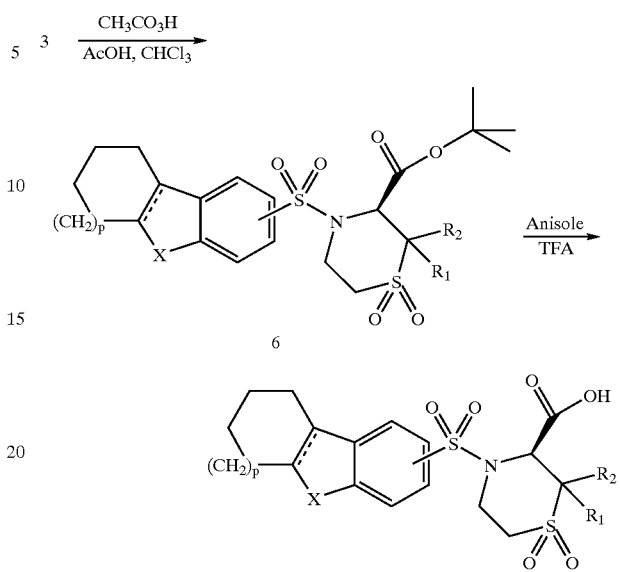

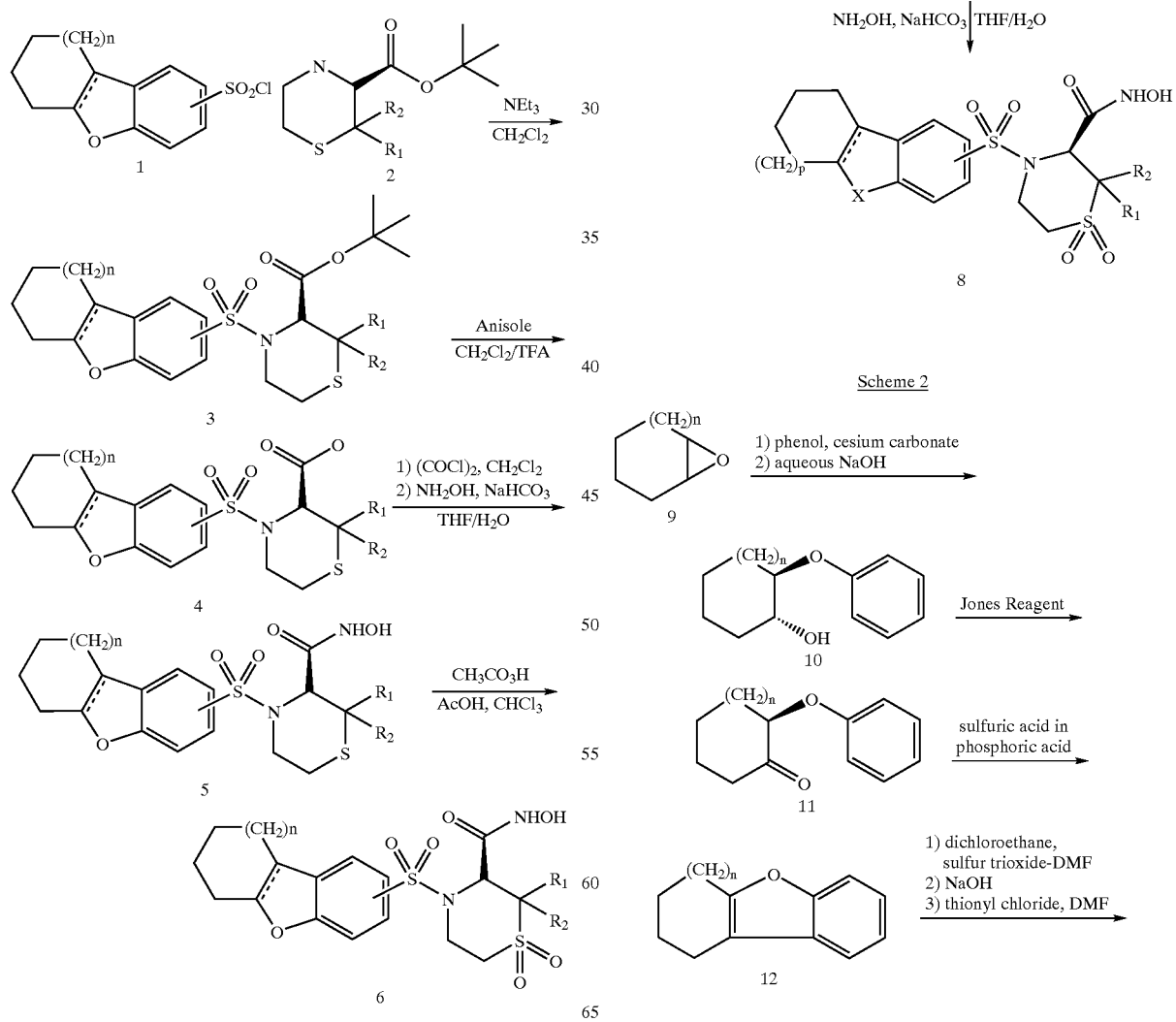

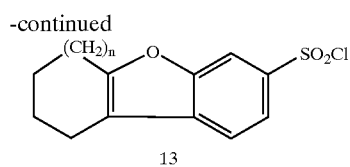

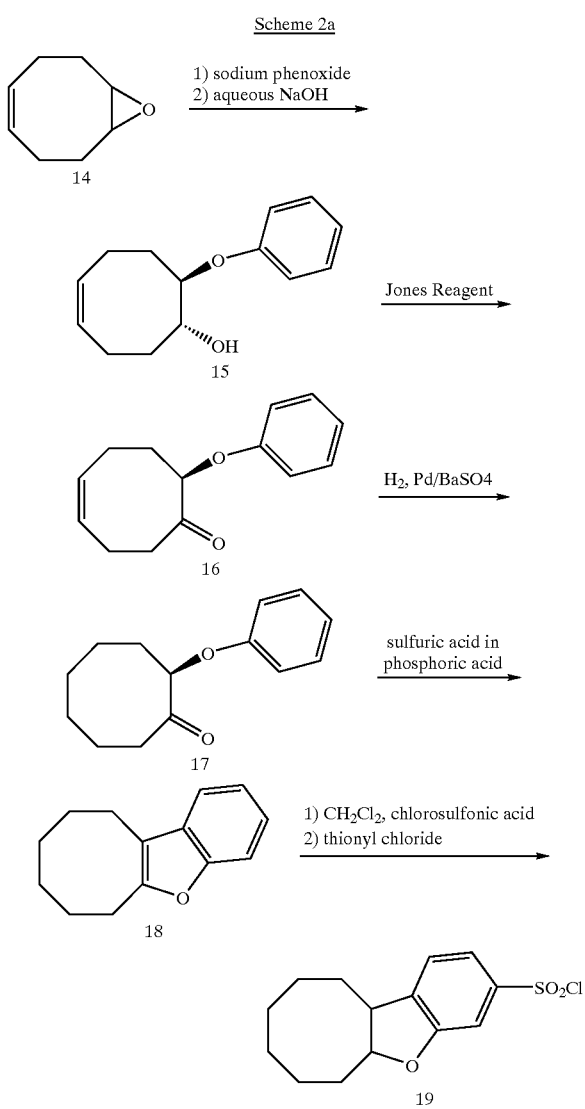

It may be desirable to derivatize certain reactive functional groups during chemical reactions in order to avoid unwanted side reactions. Groups such as carboxylic acids, amines and hydroxy groups generally are protected with any of a number of common protecting groups that can be readily removed when desired. The use of protecting groups in organic synthesis is fully described by Greene and Wuts in *Protecting Groups in Organic Synthesis,* (John Wiley & Son Press, 2$^{nd}$ edition), which is incorporated herein by reference. Typical amino acid hydroxy protecting groups include acyl groups such as formyl, acetyl, and benzoyl. Typical protecting groups for carboxylic acids include ester-forming groups such as tert-butyl, 2,2,2-trichloroethyl, and benzyl. Other common protecting groups include tert.-butoxycarbonyl (BOC) and trimethylsilyl.

The following detailed examples further illustrate the synthesis of typical invention compounds of Formula 1. The examples are representative only, and are not to be construed as limiting the invention in any respect. All references cited herein are incorporated by reference.

EXAMPLE 1

6,7,8,9-Tetrahydro-dibenzofuran-3-sulfonyl Chloride (a) To a solution of sodium phenoxide (52.1 g, 0.306 mol) in water (300 mL) was added cyclohexene oxide (10 g, 0.102 mol). The solution was refluxed for 16 hours, cooled to room temperature, and diluted with ethyl acetate (300 mL). The organic phase was separated and washed with aqueous sodium hydroxide (1 M), water, and dried over MgSO$_4$. The drying agent was filtered, and the filtrate was concentrated in vacuo. The crude liquid obtained was purified using silica gel chromatography (elution with hexane/ethyl acetate) to give the alcohol as a colorless liquid (13.6 g, 69%). $^1$HNMR (CDCl$_3$) δ 7.3 (m, 2H), 6.9 (m, 3H), 4.0 (m, 1H), 3.7 (m, 1H), 2.6 (s, 1H), 2.2 (m, 2H), 1.8 (m, 2H), 1.5–1.2 (m, 4H) ppm.

(b) The alcohol prepared in Step (a) (13.6 g, 70.9 mmol) was diluted with acetone (260 mL), cooled in an ice bath, and treated dropwise with Jones Reagent (7 mL, 2 M solution). The dark solution was stirred for 4.5 hours in an ice bath, then poured over ice. The mixture was diluted with ethyl ether (200 mL), mixed thoroughly, followed by separation of the ethereal solution. The solution was washed with saturated sodium bicarbonate, brine, and dried over sodium sulfate. The solvent was concentrated, and the crude liquid was triturated with petroleum ether to give the ketone as a colorless crystalline solid (10.2 g, 76%). $^1$HNMR (CDCl$_3$) δ 7.3 (m, 2H), 6.9 (m, 1H), 6.8 (m, 2H), 4.7 (m, 1H), 2.6 (m, 1H), 2.4–2.3 (m, 2H), 2.0 (m, 3H), 1.8 (m, 3H) ppm.

(c) To a solution of sulfuric acid (20 mL) in phosphoric acid (60 mL) cooled in an ice bath was added the ketone prepared in Step (b) (10.2 g, 53.6 mmol). The reaction mixture was gradually warmed to room temperature and was stirred for 4 hours. The mixture was poured over ice, then diluted with ethyl ether (300 mL). The organic phase was separated and washed with saturated sodium bicarbonate, brine, and dried over MgSO$_4$. The solution was filtered, and the filtrate was concentrated in vacuo. The crude product was passed through a pad of silica gel eluting with hexane to give the tetrahydrodibenzofuran (5.72 g, 61%) as a viscous liquid. $^1$HNMR (CDCl$_3$) δ 7.4 (m, 2H), 7.2 (m, 2H), 2.8 (m, 2H), 2.7 (m, 2H), 2.0–1.8 (m, 4H) ppm.

(d) The tetrahydrodibenzofuran (5.7 g, 33.1 mmol) prepared in Step (c) was diluted with dichloroethane (100 mL) followed by the addition of sulfur trioxide-DMF (16.3 g). The reaction mixture was refluxed for 3 hours and stirred at room temperature for overnight. The solvent was removed in vacuo, and the residue was taken up in water (300 mL). The solution was made basic (pH 12) with sodium hydroxide pellets affording the sulfonic acid sodium salt (4.5 g) on cooling. A portion of the salt (2 g, 7.24 mmol) was suspended in toluene (25 mL) followed by the dropwise addition of thionyl chloride (3.4 g, 28.9 mmol). One drop of DMF was added as a catalyst. The reaction mixture was refluxed overnight, cooled, and filtered. The filtrate was concentrated in vacuo, and the product obtained was suspended in hexane/ethyl acetate (9:1) to give the title sulfonyl chloride as a pale yellow solid (1.2 g). $^1$HNMR (CDCl$_3$) δ 8.1 (s, 1H), 7.9 (d, 1H), 7.6 (d, 1H), 2.8 (m, 2H), 2.7 (m, 2H), 2.0–1.8 (m, 4H) ppm.

EXAMPLE 2

(S)-2,2-Dimethyl-4-(6,7,8,9-tetrahydro-dibenzofuran-3-sulfonyl)thiomorpholine-3-carboxylic acid 1,1-dimethyl Ester To a dichloromethane solution of 6,7,8,9-tetrahydro-dibenzofuran-3-sulfonyl chloride (0.75 g, 2.77 mmol/40 mL CH$_2$Cl$_2$) and 3(S)-2,2-dimethyl-3-thiomorpholine carboxylic acid, 1,1-dimethylethyl ester hydrochloride (0.74 g, 2.77 mmol) was added triethylamine (0.8 mL). The solution was stirred at room temperature overnight, then partitioned with water. The organic layer was washed with brine, dried (MgSO$_4$), filtered and concentrated. The crude product was purified by silica gel chromatography (elution with 90% hexane/10% ethyl acetate) to give 0.71 g of the t-butyl ester. $^1$HNMR (CDCl$_3$) δ 7.8 (s, 1H), 7.5 (d, 1H), 7.4 (d, 1H), 4.3 (s, 1H), 4.1 (d, 1H), 3.9 (t, 1H), 2.8 (m, 2H), 2.6 (m, 2H), 1.9 (m, 2H), 1.8 (m, 2H), 1.6 (s, 3H), 1.3 (s, 3H), 1.2 (s, 9H) ppm.

EXAMPLE 3

(S)-2,2-Dimethyl-4-(6,7,8,9-tetrahydro-dibenzofuran-3-sulfonyl)thiomorpholine-3-carboxylic Acid

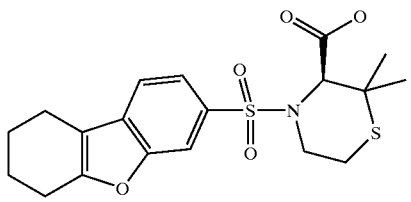

The ester obtained in Example 1 (0.7 g, 1.5 mmol) was dissolved in dichloromethane (10 mL) followed by the addition of one equivalent of anisole (0.16 g, 1.5 mmol) and trifluoroacetic acid (1 mL). The solution was stirred at room temperature overnight and concentrated in vacuo. The crude product was recrystallized from hexane/ethyl acetate to give 0.51 g of (S)-2,2-dimethyl-4-(6,7,8,9-tetrahydro-dibenzofuran-3-sulfonyl)thiomorpholine-3-carboxylic acid. $^1$HNMR (DMSO-d$_6$) δ 7.8 (s, 1H), 7.6 (d, 1H), 7.5 (d, 1H), 4.3 (s, 1H), 3.9 (d, 1H), 3.7 (tt, 1H), 2.9 (tt, 1H), 2.7 (m, 2H), 2.6 (m, 2H), 2.5 (d, 1H), 1.4 (s, 3H), 1.3 (s, 3H) ppm.

EXAMPLE 4

(S)-2,2-Dimethyl-4-(6,7,8,9-tetrahydro-dibenzofuran-3-sulfonyl)thiomorpholine-3-carboxylic Hydroxamide A dichloromethane solution of the acid synthesized in Example 2 (0.40 g, 0.97 mmol/10 mL CH$_2$Cl$_2$) was treated with oxalyl chloride (0.15 g, 1.2 mmol) and catalytic N,N-dimethylformamide under an atmosphere of nitrogen. After stirring at room temperature for 30 minutes, the solution was concentrated in vacuo. The crude acid chloride was dissolved in tetrahydrofuran and added to a tetrahydrofuran (20 mL)/water (2 mL) solution containing hydroxylamine hydrochloride (0.68 g, 0.77 mmol) and sodium bicarbonate (1.23 g, 14.6 mmol). The reaction mixture was stirred at room temperature overnight, then concentrated in vacuo. The crude product was diluted with ethyl acetate and washed with water, brine, dried (MgSO$_4$) and concentrated. The resulting residue was recrystallized from hexane/ethyl acetate to give 0.14 g of the title compound. $^1$HNMR (DMSO-d$_6$) δ 8.8 (s, 1H), 7.8 (s, 1H), 7.6 (d, 1H), 7.5 (d, 1H), 4.1 (s, 1H), 3.9 (d, 1H), 3.8 (d, 1H), 2.9 (tt, 1H), 2.7 (m, 2H), 2.6 (m, 2H), 2.6 (d, 1H), 1.9 (m, 2H), 1.8 (m, 2H), 1.4 (s, 3H), 1.1 (s, 3H) ppm.

EXAMPLE 5

2,2-Dimethyl-1,1-dioxo-4-(6,7,8,9-tetrahydro-5H-10-oxa-benzo{a}azulene-2-sulfonyl)-11$^6$-thiomorpholine-3-carboxylic Acid 1,1-dimethylethyl Ester (a) A solution of phenol (2.95 g, 0.031 mol) in water (75 mL) was treated with cesium carbonate (10.2 g, 0.031 mol) and cycloheptene oxide (3.91 g, 0.034 mol). The reaction mixture was refluxed for overnight, cooled, and diluted with diethyl ether (100 mL). The organic phase was washed with aqueous sodium hydroxide (1 M), brine, and dried over sodium sulfate. The solution was filtered and concentrated in vacuo. The crude product was passed through a pad of silica gel (elution with hexane/ethyl acetate) to give 2.1 g (33%) of a wax-like solid. $^1$HNMR (CDCl$_3$) δ 7.3 (m, 2H), 6.9 (m, 3H), 4.1(m, 1H), 3.9 (m, 1H), 2.0 (m, 2H), 1.8–1.4 (m, 8H) ppm.

(b) The alcohol prepared in Step (a) (1.7 g, 8.2 mmol) was diluted with acetone (50 mL), cooled in an ice bath, and treated dropwise with Jones Reagent (7 mL, 2 M solution). The dark solution was stirred for 2 hours in an ice bath, then poured over ice. The mixture was diluted with ethyl ether (100 mL), mixed thoroughly, followed by separation of the ethereal solution. The solution was washed with saturated sodium bicarbonate, brine, and dried over sodium sulfate. The solvent was concentrated, and the crude liquid was passed through a pad of silica gel (elution with hexane/ethyl acetate) to give 1.3 g (81%) of the ketone as a colorless liquid. $^1$HNMR (CDCl$_3$) δ 7.3 (m, 2H), 6.9 (m, 1H), 6.8 (m, 2H), 4.8 (m, 1H), 2.5 (m, 2H), 2.1–1.9 (m, 4H), 1.7–1.5 (m, 4H) ppm.

(c) The ketone prepared in Step (b) (1.3 g, 6.36 mmol) was added dropwise to a cold solution of phosphoric acid (9 mL)/sulfuric acid (3 mL). The reaction mixture warmed to room temperature and was stirred for 4 hours. The solution was poured over ice and washed with diethyl ether. The ether solution was washed with saturated sodium bicarbonate, brine, dried (Na$_2$SO$_4$), and filtered. The product was purified using silica gel chromatography (elution with hexane/tetrahydrofuran) to give the cyclized compound (1 g, 85%) as a colorless liquid. $^1$HNMR (CDCl$_3$) δ 7.4 (m, 2H), 7.1 (m, 2H), 2.9 (m, 2H), 2.7 (m, 2H), 1.8 (m, 6H) ppm.

(d) To a solution of the heterocycle prepared in Step (c) (1 g, 5.4 mmol) in dichloroethane was added sulfur trioxide-DMF (2.77 g). The solution was refluxed for 2 hours, cooled, and concentrated in vacuo. The resulting residue was dissolved in water (25 mL) and made basic (pH 12) using sodium hydroxide pellets. Crystallization of the sulfonic acid sodium salt occurred on cooling. The compound was filtered and oven-dried. The salt (1.05 g, 3.64 mmol) was suspended in toluene (25 mL) followed by the addition of thionyl chloride (2.2 g, 18.2 mmol). The mixture was refluxed overnight, cooled, and concentrated. The resulting viscous liquid was triturated with petroleum ether, the solvent was decanted and refrigerated. The resulting white precipitate (0.64 g, 43%) was collected by filtration. $^1$HNMR (CDCl$_3$) δ 8.0 (s, 1H), 7.9 (d, 1H), 7.6 (d, 1H), 3.0 (m, 2H), 2.7 (2H), 1.8 (m, 6H) ppm.

(e) The sulfonyl chloride isolated in Step (d) (0.64 g, 2.28 mmol) was added to a solution of 3(S)-2,2-dimethyl-3-thiomorpholine carboxylic acid, 1,1dimethylethyl ester (0.61 g, 2.28 mmol), and triethylamine (0.46 g, 4.56 mmol) in dichloromethane (40 mL). The solution was stirred at room temperature for overnight, at which time the solution was diluted with aqueous HCl (20 mL). The organic phase was separated, dried (MgSO$_4$), filtered, and concentrated. The resulting liquid was triturated with hexane affording a white solid that was purified using silica gel chromatography (elution with hexane/ethyl acetate) to give 0.54 g (41%) of 2,2-dimethyl-1,1-dioxo-4-(6,7,8,9-tetrahydro-5H-10-oxa-benzo{a}azulene-2-sulfonyl)-11$^6$-thiomorpholine-3-carboxylic acid 1,1-dimethylethyl ester. $^1$HNMR (CDCl$_3$) δ 7.7 (s, 1H), 7.6

(d, 1H), 7.4 (d, 1H), 4.4(s, 1H), 4.1 (d, 1H), 3.8 (m, 1H), 3.1 (m, 1H), 2.9 (m, 2H), 2.7 (m, 2H), 2.4 (d, 1H), 1.9–1.7 (m, 6H), 1.6 (s, 3H), 1.3 (s, 3H), 1.2 (s, 9H) ppm.

EXAMPLE 6
2,2-Dimethyl-1,1-dioxo-4-(6,7,8,9-tetrahydro-5H-10-oxabenzo{a}azulene-2-sulfonyl)-11$^6$-thiomorpholine-3-carboxylic Acid The ester from Example 5 (0.48 g, 1 mmol) was diluted with dichloromethane (10 mL) and trifluoroacetic acid (1 mL) and stirred at room temperature for overnight. The solution was poured over ice and the resulting solid was collected by filtration and dried in vacuo to give 2,2-dimethyl-1,1-dioxo-4-(6,7,8,9-tetrahydro-5H-10-oxabenzo{a}azulene-2-sulfonyl)-11$^6$-thiomorpholine-3-carboxylic acid (0.1 g, 24%) as a cream colored solid. $^1$HNMR (DMSO-d$_6$) δ 7.8 (s, 1H), 7.7 (d, 1H), 7.5 (d, 1H), 4.2 (s, 1H), 3.9 (d, 1H), 3.6 (t, 1H), 2.9 (m, 2H), 2.7 (m, 2H), 2.5 (m, 1H), 1.9–1.7 (m, 8H), 1.4 (s, 3H), 1.2 (s, 3H) ppm.

EXAMPLE 7
2,2-Dimethyl-1,1-dioxo-4-(6,7,8,9-tetrahydro-5H-10-oxabenzo{a}azulene-2-sulfonyl)-11$^6$-thiomorpholine-3-carboxylic Acid Hydroxyamide A dichloromethane solution of the acid prepared in Example 6 (0.075 g, 0.18 mmol/10 mL) was treated with oxalyl chloride (0.05 mL) and DMF (1 drop) at room temperature. After stirring for 30 minutes, the solution was concentrated in vacuo. The crude acid chloride was re-dissolved in tetrahydrofuran and added to a solution of hydroxylamine hydrochloride and sodium bicarbonate in aqueous tetrahydrofuran. The reaction mixture was stirred for overnight, concentrated in vacuo, and re-dissolved in ethyl acetate. The solution was washed with water, brine, and dried over MgSO$_4$. The drying agent was filtered, and the filtrate was concentrated. The residue was recrystallized from hexanelethyl acetate to give 0.013 g (17%) of the title compound as a white solid. Cl-MS [M+1] 439.2.

EXAMPLE 8
4-(5,6,7,8,9,10-Hexahydro-11-oxa-cycloocta{a}indene-2-sulfonyl)-2,2-dimethylthiomorpholine-3-carboxylic Acid 1,1-dimethylethyl Ester (a) The cyclooctene oxide (7.78 g, 0.063 mol) was added dropwise to a solution of sodium phenoxide (21.3 g, 0.125 mol) in water (200 mL). The reaction mixture was refluxed overnight, cooled, and diluted with diethyl ether (200 mL). The organic phase was separated, washed with saturated sodium bicarbonate, and brine. The solution was dried (MgSO$_4$) and concentrated to give a colorless liquid. The crude product was purified using silica gel chromatography (elution with hexane/ethyl acetate) to give the alcohol as a colorless liquid (4.2 g, 31%). $^1$HNMR (CDCl$_3$) δ 7.3 (m, 2H), 6.9 (m, 3H), 5.6 (m, 2H), 4.4 (m, 1H), 4.1 (m, 1H), 2.5 (m, 2H), 2.3–2.1 (m, 4H), 1.8 (m, 2H) ppm.

(b) The alcohol prepared in Step (a) (4.2 g, 0.019 mol) was diluted with acetone (150 mL), cooled in an ice bath, and treated dropwise with Jones Reagent (13 mL, 2 M solution). The dark solution was stirred for 2 hours in an ice bath, then poured over ice. The mixture was diluted with ethyl ether (100 mL), mixed thoroughly, followed by separation of the ethereal solution. The solution was washed with saturated sodium bicarbonate, brine, and dried over sodium sulfate. The solvent was concentrated, and the crude liquid was passed through a pad of silica gel (elution with hexane/ethyl acetate) to give 3.6 g (80%) of the ketone as a colorless liquid. $^1$HNMR (CDCl$_3$) δ 7.3 (m, 2H), 7.0 (m, 1H), 6.9 (m, 2H), 5.7 (m, 2H), 4.7 (m, 1H), 3.1 (m, 1H), 2.9 (m, 2H), 2.3 (m, 1H), 2.1–1.8 (m, 6H) ppm.

(c) The unsaturated ketone from Step (b) (2.81g, 0.013 mol) was diluted with THF (100 mL) and hydrogenated under H$_2$ at 50 psi in the presence of 10% Pd/BaSO$_4$ (0.5 mg). The reaction mixture was mixed in a Parr Shaker for 19 hours, then filtered. The filtrate was concentrated in vacuo to give a colorless liquid (2.8 g, 100%). $^1$HNMR (CDCl$_3$) δ 7.3 (m, 2H), 6.9 (m, 1H), 6.8 (m, 2H), 4.7 (m, 1H), 3.7 (m, 2H), 2.6 (m, 1H), 2.3–2.1 (m, 3H), 1.8 (m, 2H), 1.6 (m, 2H), 1.3 (m, 2H) ppm.

(d) To a phosphoric acid (18 mL)/sulfuric acid (6 mL) solution was added at room temperature the ketone (2.8 g, 0.013 mol) prepared in Step (c). The reaction mixture was stirred for 6 hours then poured over ice. The mixture was diluted with diethyl ether, the organic phase was separated and washed with saturated sodium bicarbonate, brine, and dried over MgSO$_4$. The solution was filtered, and the filtrate was concentrated to give a pink liquid. The crude product was passed through a pad of silica gel (elution with hexane/ethyl acetate) to give the cyclized derivative (1.9 g, 73%). $^1$HNMR (CDCl$_3$) δ 7.4 (m, 2H), 7.2 (m, 2H), 2.9 (m, 2H), 2.8 (m, 2H), 2.9–2.7 (m, 4H), 1.5 (m, 4H) ppm.

(e) The tricycle from Step (d) (0.5 g, 2.49 mmol) was diluted with chloroform (20 mL), cooled in an ice bath, followed by the addition of chlorosulfonic acid (0.36 g, 3.12 mmol). The reaction mixture gradually warmed to room temperature and was stirred for overnight. The solvent was concentrated in vacuo, and the resulting liquid was partitioned between water and diethyl ether. The aqueous phase was separated and concentrated in vacuo to give a maroon colored liquid. The crude sulfonic acid was suspended in toluene (25 mL) followed by the addition of thionyl chloride (1.5 g, 12.6 mmol). The mixture was refluxed for 4 hours, cooled, and concentrated. The resulting liquid was passed through a pad of silica gel (elution with hexane/ethyl acetate) to give the sulfonyl chloride (0.42 g, 57%) as a pale yellow liquid. $^1$HNMR (CDCl$_3$) δ 8.1 (s, 1H), 7.9 (d, 1H), 7.6 (d, 1H), 3.0 (m, 2H), 2.8 (m, 2H), 2.9 (m, 2H), 2.8 (m, 2H), 1.5 (m, 4H) ppm.

(f) The sulfonyl chloride isolated in Step (e) (0.30 g, 1 mmol) was added to a solution of 3(S)-2,2-dimethyl-3-thiomorpholine carboxylic acid, 1,1-dimethylethyl ester (0.24 g, 1.05 mmol) and triethylamine (0.106 g, 1.05 mmol) in dichloromethane (20 μL). The solution was stirred at room temperature for 3 days, at which time the solution was diluted with aqueous HCl (20 mL). The organic phase was separated, dried (MgSO$_4$), filtered and concentrated. The resulting liquid was triturated with hexane affording a white solid of 4-(5,6,7,8,9,10-hexahydro-11-oxa-cycloocta{a}indene-2-sulfonyl)-2,2-dimethylthiomorpholine-3-carboxylic acid 1,1-dimethylethyl ester (0.195 g, 41%). $^1$HNMR (CDCl$_3$) δ 7.8 (s, 1H), 7.6 (d, 1H), 7.5 (d, 1H), 4.3 (s, 1H), 4.1 (m, 1H), 3.9 (m, 1H), 3.1 (m, 1H), 2.9 (m, 2H), 2.8 (m, 2H), 2.4 (m, 1H), 1.9–1.7 (m, 4H), 1.5 (m, 4H), 1.4 (s, 3H), 1.3 (s, 3H), 1.1 (s, 9H) ppm.

EXAMPLE 9
4-(5,6,7,8,9,10-Hexahydro-11-oxa-cycloocta{a}indene-2-sulfonyl)-2,2-dimethylthiomorpholine-3-carboxylic acid The ester from Example 8 (0.184 g, 0.38 mmol) was diluted with trifluoroacetic acid (5 mL) and stirred at room temperature for overnight. The solution was poured over ice, and the resulting solid was collected by filtration and dried in vacuo to give the acid (0.133 g, 80%) as a cream colored solid. $^1$HNMR (DMSO-d$_6$) δ 12.7 (bs, 1H), 7.8 (s, 1H), 7.7 (d, 1H), 7.5 (d, 1H), 4.3 (s, 1H), 3.9 (m, 1H), 3.6 (m, 1H), 2.9 (m, 3H), 2.8 (m, 2H), 2.3 (m, 1H), 1.8 (m, 2H), 1.7 (m, 2H), 1.5 (m, 2H), 1.49 (s, 3H), 1.2 (s, 3H) ppm.

EXAMPLE 10
4-(5,6,7,8,9,10-Hexahydro-11-oxa-cycloocta{a}indene-2-sulfonyl)-2,2-dimethylthiomorpholine-3-carboxylic Acid Hydroxyamide This compound is made by the same procedures as found in Example 7 with 4-(5,6,7,8,9,10-hexahydro-11-oxa-cycloocta{a}indene-2-sulfonyl)-2,2-dimethylthiomorpholine-3-carboxylic acid substituted for 2,2-dimethyl-1,1-dioxo-4-(6,7,8,9-tetrahydro-5H-10-oxa-benzo{a}azulene-2-sulfonyl)-11$^6$-thiomorpholine-3-carboxylic acid.

EXAMPLE 11
4-(2,3-Dihydro-1H-8-oxa-cyclopenta[a]indene-6-sulfonyl)-2,2-dimethylthiomorpholine-3-carboxylic Acid Hydroxyamide This compound is prepared by the method of Examples 2–4 by replacing 6,7,8,9-tetrahydro-dibenzofuran-3-sulfonyl chloride with 2,3,3a,8a-tetrahydro-1H-8-oxa-cyclopenta[α]indene-6-sulfonyl chloride, which has the structure shown immediately below.

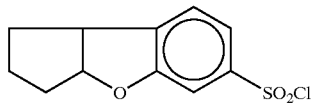

General Procedure for Preparing Thiomorpholine Sulfone Derivatives:

To a chloroform solution of the hydroxyamide prepared in Example 4 is added peracetic acid. The solution is stirred at room temperature overnight, at which time the solvent is concentrated and the product recrystallized from hexane/ethyl acetate to yield the title compound.

Utilizing the experimental conditions described above, the following compounds are prepared:

EXAMPLE 12
(S)-2,2-Dimethyl-1,1-dioxo-4-(6,7,8,9-tetrahydro-dibenzofuran-3-sulfonyl)-11$^6$-thiomorpholine-3-carboxylic acid hydroxyamide

EXAMPLE 13
4-(2,3-Dihydro-1H-8-oxa-cyclopenta[a]indene-6-sulfonyl)-2,2-dimethyl-1,1-dioxo-11$^6$-thiomorpholine-3-carboxylic acid hydroxyamide

EXAMPLE 14
2,2-Dimethyl-1,1-dioxo-4-(6,7,8,9-tetrahydro-5H-10-oxa-benzo[a]azulene-2-sulfonyl)-11$^6$-thiomorpholine-3-carboxylic acid hydroxyamide

EXAMPLE 15
4-(5,6,7,8,9,10-Hexahydro-11-oxa-cycloocta[a]indene-2-sulfonyl)-2,2-dimethyl-1,1-dioxo-11$^6$-thiomorpholine-3-carboxylic Acid Hydroxyamide The invention compounds of Formula I have been evaluated in standard assays for their ability to inhibit the catalytic activity of various MMP enzymes. The assays used to evaluate the biological activity of the invention compounds are well known and routinely used by those skilled in the study of MMP inhibitors and their use to treat clinical conditions.

The assays measure the amount by which a test compound reduces the hydrolysis of a thiopeptolide substrate catalyzed by a matrix metalloproteinase enzyme. Such assays are described in detail by Ye et al., in *Biochemistry*, 1992;31 (45):11231–11235, which is incorporated herein by reference.

Thiopeptolide substrates show virtually no decomposition or hydrolysis at or below neutral pH in the absence of a matrix metalloproteinase enzyme. A typical thiopeptolide substrate commonly utilized for assays is Ac-Pro-Leu-Gly-thioester-Leu-Leu-Gly-OEt. A 100 μL assay mixture will contain 50 mM of N-2-hydroxyethylpiperazine-N'-2-ethanesulfonic acid buffer ("HEPES") at pH 7.0, 10 mM CaCl$_2$, 100 μM thiopeptolide substrate, and 1 mM 5,5'-dithio-bis-(2-nitro-benzoic acid) (DTNB). The thiopeptolide substrate concentration may be varied from, for example, 10 to 800 μM to obtain Km and Kcat values. The change in absorbance at 405 nm is monitored on a Thermo Max microplate reader (Molecular Devices, Menlo Park, Calif.) at room temperature (22° C.). The calculation of the amount of hydrolysis of the thiopeptolide substrate is based on $E_{412}=13600$ $M^{-1}$ $cm^{-1}$ for the DTNB-derived product 3-carboxy-4-nitrothiophenoxide. Assays are carried out with and without matrix metalloproteinase inhibitor compounds, and the amount of hydrolysis is compared for a determination of inhibitory activity of the test compounds.

Several representative compounds have been evaluated for their ability to inhibit various matrix metalloproteinase enzymes. Table 1 below presents inhibitory activity for compounds from various classes. In Table 1, MMP-1FL refers to full length interstitial collagenase; MMP-2FL refers to full length Gelatinase A; MMP-3CD refers to the catalytic domain of stromelysin-1; MMP-7FL refers to full length matrilysin; MMP-9FL refers to full length Gelatinase B; MMP-13CD refers to the catalytic domain of collagenase 3; and MMP-14CD refers to the catalytic domain of MMP-14. Test compounds were evaluated at various concentrations in order to determine their respective IC$_{50}$ values, the micromolar concentration of compound required to cause a 50% inhibition of the catalytic activity of the respective enzyme.

It should be appreciated that the assay buffer used with MMP-3CD was 50 mM of 2-morpholinoethanesulfonic acid monohydrate ("MES") at pH 6.0, rather than the HEPES buffer at pH 7.0 described above.

TABLE 1

| Example | MMP-1FL | MMP-2FL | MMP-3CD | MMP-7FL | MMP-9FL | MMP-13CD | MMP-14CD |
|---|---|---|---|---|---|---|---|
| | | | $IC_{50}$ ($\mu$M) | | | | |
| 3 | 6.9 | 0.39 | 0.039 | 100 | 54 | 1.31 | 0.15 |
| 4 | 0.069 | 0.082 | 0.009 | 0.23 | 0.21 | 0.012 | 0.052 |
| 6 | 40 | 0.6 | 0.037 | 41 | 70 | 2.1 | 0.093 |
| 7 | 0.97 | 0.22 | 0.015 | 0.42 | 0.45 | 0.0062 | 0.053 |

The foregoing data establish that the invention compounds of Formula I are potent inhibitors of a broad spectrum of MMP enzymes. Because of this potent inhibitory activity, the invention compounds are especially useful to treat diseases mediated by the MMP enzymes, diseases such as cancer, rheumatoid arthritis, osteoarthritis, atherosclerosis, and congestive heart failure.

Administration of a compound of the present invention, or a pharmaceutically acceptable salt thereof, to treat a disease mediated by an MMP enzyme is preferably, although not necessarily, accomplished by administering the invention compound, or the salt thereof, in a pharmaceutical dosage form.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I. The active compound generally is present in a concentration of about 5% to about 95% by weight of the formulation.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, preferably 10 mg to 100 mg according to the particular application and the potency of the active component. The composition can, if desired, also contain other compatible therapeutic agents.

In therapeutic use as agents to inhibit a matrix metalloproteinase enzyme for the treatment of atherosclerotic plaque rupture, aortic aneurism, heart failure, restenosis, periodontal disease, corneal ulceration, cancer metastasis, tumor angiogenesis, arthritis, or other autoimmune or inflammatory disorders dependent upon breakdown of connective tissue, the compounds utilized in the pharmaceutical method of this invention are administered at a dose that is effective to inhibit the hydrolytic activity of one or more matrix metalloproteinase enzymes. The initial dosage of about 1 mg to about 100 mg per kilogram daily will be effective. A daily dose range of about 25 mg to about 75 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired. Typical dosages will be from about 0.1 to about 500 mg/kg, and ideally about 25 to about 250 mg/kg, such that it will be an amount which is effective to treat the particular disease being prevented or controlled.

The following examples illustrate typical pharmaceutical compositions provided by the invention.

COMPOSITION EXAMPLE 1

Tablet Formulation

| Ingredient | Amount (mg) |
| --- | --- |
| Compound of Example 2 | 25 |
| Lactose | 50 |
| Corn starch (for mix) | 10 |
| Corn starch (paste) | 10 |
| Magnesium stearate (1%) | 5 |
| Total | 100 |

The tricyclicsulfonamide of Example 2, lactose, and corn starch (for mix) are blended to uniformity. The corn starch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a human from one to four times a day for treatment of atherosclerosis and arthritis.

COMPOSITION EXAMPLE 2

Preparation for Oral Solution

| Ingredient | Amount |
| --- | --- |
| Compound of Example 3 | 400 mg |
| Sorbitol solution (70% N.F.) | 40 mL |
| Sodium benzoate | 20 mg |
| Saccharin | 5 mg |
| Red dye | 10 mg |
| Cherry flavor | 20 mg |
| Distilled water q.s. | 100 mL |

The sorbitol solution is added to 40 mL of distilled water, and the tricyclicsulfonamide of Example 3 is dissolved therein. The saccharin, sodium benzoate, flavor, and dye are added and dissolved. The volume is adjusted to 100 mL with distilled water. Each milliliter of syrup contains 4 mg of invention compound.

COMPOUND EXAMPLE 3

Parenteral Solution

In a solution of 700 mL of propylene glycol and 200 mL of water for injection is suspended 20 g of the compound of Example 8. After suspension is complete, the pH is adjusted to 6.5 with 1 N sodium hydroxide, and the volume is made up to 1000 mL with water for injection. The formulation is sterilized, filled into 5.0 mL ampoules each containing 2.0 mL, and sealed under nitrogen.

As matrix metalloproteinase inhibitors, the compounds of Formula I are useful as agents for the treatment of multiple sclerosis. They are also useful as agents for the treatment of atherosclerotic plaque rupture, restenosis, periodontal disease, corneal ulceration, treatment of burns, decubital ulcers, wound repair, heart failure, cancer metastasis, tumor angiogenesis, arthritis, and other inflammatory disorders dependent upon tissue invasion by leukocytes.

It should be appreciated that in all invention embodiments described above or in the claims below, whenever an R group such as, for example, $R^1$, $R^2$, or $R^3$, is used more than once to define an invention compound, each use of the R group is independent of any other use of that same R group or, for that matter, any other R group, unless otherwise specified.

What is claimed is:

1. A compound of Formula I

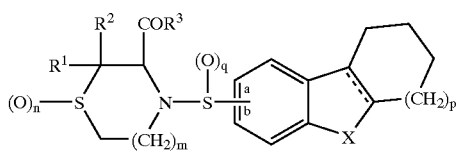

or a pharmaceutically acceptable salt thereof,
wherein:
the sulfur atom bearing $(O)_q$ is bonded to the benzo ring at position a or position b;
$R^1$ and $R^2$ independently are hydrogen, $C_1$–$C_6$ alkyl, $C_1$–$C_6$ alkoxy, $C_2$–$C_6$ alkenyl, $C_2$–$C_6$ alkynyl, or $(CH_2)_t$ aryl;
$R^3$ is NHOH or $OR^4$;
$R^4$ is H, $C_1$–$C_6$ alkyl, or $(CH_2)_t$ aryl;
X is O or $S(O)_n$;
each n and q independently are 0, 1, or 2;
m is 0, 1, or 2;
p is 0, 1, 2, or 3;
each t is an integer from 0 to 6; and
— is absent or is a bond.

2. A compound of Formula II

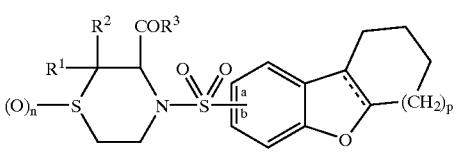

or a pharmaceutically acceptable salt thereof,
wherein $R^1$ and $R^2$ independently are H or $C_1$–$C_6$ alkyl;
$R^3$ is NHOH or OH;
the sulfonyl diradical is bonded to the benzo ring at position a or position b;
n is 0, 1, or 2;
p is 1 or 2; and
— is absent or is a bond.

3. A compound of Formula III

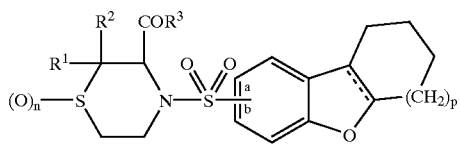

or a pharmaceutically acceptable salt thereof,
wherein R$^1$ and R$^2$ independently are H or C$_1$–C$_6$ alkyl;
R$^3$ is NHOH or OH;
the sulfonyl diradical is bonded to the benzo ring at position b;
n is 0, 1, or 2;
p is 1 or 2; and
— is absent or is a bond.

4. The compound of claim 1 wherein R$^3$ is OH.
5. The compound of claim 1 wherein R$^3$ is NHOH.
6. The compound of claim 1 wherein — is a bond.
7. The compound of claim 1 wherein — is absent.
8. The compound of claim 1 wherein X is O.
9. A compound selected from:
(S)-2,2-Dimethyl-4-(6,7,8,9-tetrahydro-dibenzofuran-3-sulfonyl)-thiomorpholine-3-carboxylic acid 1,1-dimethyl ester;
(S)-2,2-Dimethyl-4-(6,7,8,9-tetrahydro-dibenzofuran-3-sulfonyl)-thiomorpholine-3-carboxylic acid;
(S)-2,2-Dimethyl-4-(6,7,8,9-tetrahydro-dibenzofuran-3-sulfonyl)-thiomorpholine-3-carboxylic hydroxamide;
4-(2,3-Dihydro-1H-8-oxa-cyclopenta[a]indene-6-sulfonyl)-2,2-dimethyl-thiomorpholine-3-carboxylic acid hydroxyamide;
2,2-Dimethyl-4-(6,7,8,9-tetrahydro-5H-10-oxa-benzo[a]azulene-2-sulfonyl)thiomorpholine-3-carboxylic acid hydroxyamide;
4-(5,6,7,8,9,10-Hexahydro-11-oxa-cycloocta[a]indene-2-sulfonyl)-2,2-dimethyl-thiomorpholine-3-carboxylic acid hydroxyamide;
(S)-2,2-Dimethyl-1,1-dioxo-4-(6,7,8,9-tetrahydro-dibenzofuran-3-sulfonyl)-11$^6$-thiomorpholine-3-carboxylic acid hydroxyamide;
4-(2,3-Dihydro-1H-8-oxa-cyclopenta[a]indene-6-sulfonyl)-2,2-dimethyl-1,1-dioxo-11$^6$-thiomorpholine-3-carboxylic acid hydroxyamide;
2,2-Dimethyl-1,1-dioxo-4-(6,7,8,9-tetrahydro-5H-10-oxa-benzo[a]azulene-2-sulfonyl)-11$^6$-thiomorpholine-3-carboxylic acid hydroxyamide; and
4-(5,6,7,8,9,10-Hexahydro-11-oxa-cycloocta[a]indene-2-sulfonyl)-2,2-dimethyl-1,1-dioxo-11$^6$-thiomorpholine-3-carboxylic acid hydroxyamide.

10. A pharmaceutical composition, comprising a compound of claim 1, or a pharmaceutically acceptable salt thereof, together with a pharmaceutically acceptable carrier, diluent, or excipient.

11. A pharmaceutical composition comprising a compound of claim 2, or a pharmaceutically acceptable salt thereof, together with a pharmaceutically acceptable carrier, diluent, or excipient.

12. A method for treating a rheumatoid arthritis, comprising administering to a patient suffering from such a disease an effective amount of a compound of claim 1, or a pharmaceutically acceptable salt thereof.

13. A method for treating a osteoarthritis, comprising administering to a patient suffering from such a disease an effective amount of a compound of claim 1, or a pharmaceutically acceptable salt thereof.

* * * * *